United States Patent [19]

Fukami et al.

[11] Patent Number: 5,424,310

[45] Date of Patent: Jun. 13, 1995

[54] SUBSTITUTED 1,2,4-TRIAZINE-3,5-DIONE DERIVATIVE AND ANTICOCCIDIAL DRUG COMPOSITION CONTAINING THE SAME AS ACTIVE COMPONENT

[75] Inventors: Harukazu Fukami, Kyoto; Masaki Hashimoto; Shinjiro Niwata, both of Ibaraki; Jun Imose, Koka; Harumoto Kawaguchi, Ayama; Toshio Takahashi, Nishinomiya, all of Japan

[73] Assignees: Suntory Limited; Shionogi & Co., Ltd., both of Osaka, Japan

[21] Appl. No.: 79,925

[22] Filed: Jun. 23, 1993

[30] Foreign Application Priority Data

Jun. 25, 1992 [JP] Japan .................. 4-167837
Jun. 8, 1993 [JP] Japan .................. 5-137605

[51] Int. Cl.6 ............... C07D 253/075; A61K 31/53
[52] U.S. Cl. ............................ 514/242; 544/182
[58] Field of Search ................. 544/182; 514/242

[56] References Cited

U.S. PATENT DOCUMENTS

| | | | |
|---|---|---|---|
| 3,912,723 | 10/1975 | Miller | 544/182 |
| 4,935,423 | 6/1990 | Lindner et al. | 544/182 |
| 4,968,795 | 11/1990 | Lindner et al. | 544/182 |
| 5,114,938 | 5/1992 | Lindner et al. | 544/182 |
| 5,214,043 | 5/1993 | Lindner et al. | 544/182 |

FOREIGN PATENT DOCUMENTS

| | | |
|---|---|---|
| 851655 | 2/1977 | Belgium . |
| 851655 | 2/1977 | Belgium . |
| 0339555B1 | 11/1984 | European Pat. Off. . |
| 0330041A2 | 8/1989 | European Pat. Off. . |
| 0377903A2 | 7/1990 | European Pat. Off. . |
| 2532363 | 2/1977 | Germany . |
| 47-9998 | 5/1972 | Japan . |
| 50-19763 | 3/1975 | Japan . |
| 1562935 | 3/1980 | United Kingdom . |

*Primary Examiner*—John M. Ford
*Attorney, Agent, or Firm*—Burns, Doane, Swecker & Mathis

[57] ABSTRACT

A substituted 1,2,4-triazine-3,5-dione derivative having the formula (I) or a salt thereof:

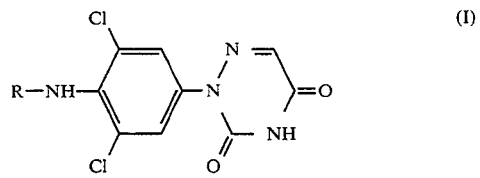

wherein R represents a 5- or 6-membered heterocyclic group which may have at least one substituent selected from the group consisting of a halogen, a lower alkyl group and a halogenated lower alkyl group, and an anticoccidial drug composition containing the same as an active component.

11 Claims, No Drawings

SUBSTITUTED 1,2,4-TRIAZINE-3,5-DIONE DERIVATIVE AND ANTICOCCIDIAL DRUG COMPOSITION CONTAINING THE SAME AS ACTIVE COMPONENT

BACKGROUND OF THE INVENTION

1. Field of the Invention

The present invention relates to a novel substituted 1,2,4-triazine-3,5-dione derivative or a salt thereof and an anti-coccidial drug composition containing the same as an active component.

2. Description of the Related Art

Coccidiosis is an infectious disease caused by protozoans belonging to coccidium. Poultry is mainly infected with *Eimeria tenella, Eimeria aceruvulina* and *Eimeria necatrix*, and suffers from various troubles such as bleeding of the gastrointerstinal tract, mortality, growth inhibition, and so forth. Poultry includes chickens, turkeys, quails and ducks. Mass outbreak of avian coccidiosis in a commercial poultry farm imparts an extremely great loss to an owner and has often become a serious problem. Accordingly, the development of an anticoccidial drug composition which is effective for prevention and remedy of coccidiosis has drawn a keen attention of those concerned in the art.

Conventionally, sulfanilamides, nitrofurans, quinolines, antithiamines and benzoamides have been put into practical application as the anticoccidial drug, and polyether-based antibiotics have been used mainly at present. However, these compounds have the drawbacks in that, although their efficacy against coccidiosis is not very high, they are toxic to hosts. Moreover, resistant strains appear in the course of continuous use of these chemicals, and their efficacy drops progressively with time. In view of these circumstances, the development of a novel anticoccidial agent which is effective for the resistant strains and at the same time, hardly imparts resistance to the strains, has been desired earnestly.

Japanese Unexamined Patent Publication (Kokai) No. 47-9998 and No. 50-19763, German Unexamined Patent Publication No. 2532363 and Belgian Unexamined Patent Publication No. 851655 disclose a compound having a basic skeletal structure expressed by the following general formula (II) as a 1,2,4-triazine-3,5-dione derivative having an anticoccidial action:

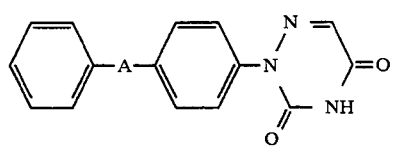

wherein A represents O, S, SO or $SO_2$. However, these compounds have not been entirely satisfactory in the aspects of the anti-coccidium action, toxicity and the appearance of resistant strains.

SUMMARY OF THE INVENTION

Accordingly, the objects of the present invention are to eliminate the above-mentioned disadvantage of the prior art and to provide a novel substituted 1,2,4-triazine-3,5-dione derivative or a salt thereof and an anticoccidial drug composition containing the same, as an active component, having a high anticoccidial activity and capable of preventing the mass outbreak of coccidiosis.

Other objects and advantage of the present invention will be apparent from the following description.

In accordance with the present invention, there is provided a substituted 1,2,4-triazine-3,5-dione derivative having the formula (I) or a salt thereof:

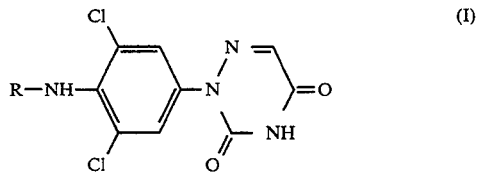

wherein R represents a 5- or 6-membered heterocyclic group which may have at least one substituent, selected from the group consisting of a halogen, a lower alkyl group and a halogenated lower alkyl group.

In accordance with the present invention, there is also provided an anticoccidial drug composition comprising an anticoccidially effective amount of at least one compound (I) mentioned above, as an active component, and a carrier therefor.

DESCRIPTION OF THE PREFERRED EMBODIMENTS

In view of the above-mentioned prior art, the inventors of the present invention have carried out intensive studies about a substituted 1,2,4-triazine-3,5-dione derivative in order to develop a medicament having an excellent anticoccidial action, and have found that a substituted 1,2,4-triazine-3,5-dione derivative having the above-mentioned general formula (I) or a salt thereof has an excellent anticoccidial action, and have thus developed an anticoccidium drug composition containing the substituted 1,2,4-triazine-3,5-dione derivative or a salt thereof as an active component and, thus, the present invention has been completed.

Namely, according to the present invention, there are provided the substituted 1,2,4-triazine-3,5-dione derivative and a salt thereof, particularly a nontoxic salt thereof. Examples of such nontoxic salts include salts of inorganic acids such as hydrogen halide acids (e.g. hydrochloric acid and hydrobromic acid), sulfuric acid and phosphoric acid, salts of organic acids such as acetic acid, propionic acid, oxalic acid, malonic acid and benzoic acid, and salts of alkali metals such as lithium sodium and potassium.

The heterocyclic group represented by R in the formula (I) includes 5-membered or 6-membered heterocyclic group containing one or two nitrogen atoms, oxygen atoms or sulfur atoms. Examples of the 5-membered heterocyclic group are isoazolyl group, oxazolyl group, thiadiazolyl group, etc, and examples of the 6-membered heterocyclic group are pyridyl group, pyrimidyl (or pyrimidinyl) group, pyrazinyl and so forth. These heterocyclic groups may be substituted by a halogen, a lower alkyl group or a halogenated lower alkyl group.

The term "halogen" represents fluorine, chlorine, bromine and iodine, and the term "lower alkyl group" represents a straight-chain or branched-chain alkyl group having 1 to 4 carbon atoms such as methyl group, ethyl group, propyl group, isopropyl group, butyl group, isobutyl group, sec-butyl group, tert-butyl group, or the like. Further, the term "halogenated lower alkyl group" represents a lower alkyl group at least one of the hydrogen atoms of which is substituted by a halogen(s), such as monofluoromethyl group, difluoromethyl group, trifluoromethyl group, 2-fluoroethyl group, 1,2-difluoroethyl group, 2,2,2-trifluoroethyl group, 1,1,2,2-tetrafluoroethyl group, perfluoroethyl group, monochloromethyl group, 2-chloroethyl group, 2,2,2-trichloroethyl group, 2,2-dibromoethyl group, or the like.

Examples of the above-mentioned 5- or -6 membered heterocyclic group which may be substituted with at least one substituent are as follows:

3-chloro-2-pyridyl, 5-chloro-2-pyridyl, 5-bromo-2-pyridyl, 5-fluoro-2-pyridyl, 3-methyl-2-pyridyl, 5-methyl-2-pyridyl, 3-trifluoromethyl-2-pyridyl, 5-trifluoromethyl-2-pyridyl, 3,5-dichloro-2-pyridyl, 3-chloro-5-methyl-2-pyridyl, 3-fluoro-5-trifluoromethyl-2-pyridyl, 3-chloro-5-trifluoromethyl-2-pyridyl, 5-chloro-3-methyl-2-pyridyl, 3,5-dimethyl-2-pyridyl, 3-methyl-5-trifluoromethyl-2-pyridyl, 5-chloro-3-trifluoromethyl-2-pyridyl, 5-methyl-3-trifluoromethyl-2-pyridyl, 3,5-ditrifluoromethyl-2-pyridyl, 4,6-ditrifluoromethyl-2-pyridyl, 4-methyl-2-pyridyl, 4-trifluoromethyl-2-pyridyl, 4,6-dimethyl-2-pyridyl, 6-methyl-2-pyridyl, 6-trifluoromethyl-2-pyridyl, 4-chloro-3-pyridyl, 5-bromo-3-pyridyl, 2-methyl-3-pyridyl, 4-methyl-3-pyridyl, 5-methyl-3-pyridyl, 6-methyl-3-pyridyl, 2-trifluoromethyl-3-pyridyl, 4-trifluoromethyl-3-pyridyl, 5-trifluoromethyl-3-pyridyl, 6-trifluoromethyl-3-pyridyl, 4-chloro-2-methyl-3-pyridyl, 2,4-dimethyl-3-pyridyl, 2,6-dimethyl-3-pyridyl, 2-methyl-4-trifluoromethyl-3-pyridyl, 2-methyl-6-trifluoromethyl- 3-pyridyl, 4-chloro-2-trifluoromethyl-3-pyridyl, 4-methyl-2-trifluoromethyl-3-pyridyl, 6-methyl-2-trifluoromethyl-3-pyridyl, 2,4-ditrifluoromethyl-3-pyridyl, 2,6-ditrifluoromethyl-3-pyridyl, 2-methyl-4-pyridyl, 2-trifluoromethyl-4-pyridyl, 3-chloro-4-pyridyl, 3-methyl-4-pyridyl, 3-trifluoromethyl-4-pyridyl, 5-chloro-4-pyridyl, 5-methyl-4-pyridyl, 5-trifluoromethyl-4-pyridyl, 3,5-dichloro-4-pyridyl, 3-chloro-5-methyl-4-pyridyl, 3-chloro-5-trifluoromethyl-4-pyridyl, 3,5-dimethyl-4-pyridyl, 3-methyl-5-trifluoromethyl-4-pyridyl, 3,5-ditrifluoromethyl-4-pyridyl, 2,6-dimethyl-4-pyridyl, 2,6-ditrifluoromethyl-4-pyridyl;

5-chloro-2-pyrimidinyl, 5-bromo-2-pyrimidinyl, 5-methyl-2-pyrimidinyl, 5-trifluoromethyl-2-pyrimidinyl, 4,6-dimethyl-2-pyrimidinyl, 4,6-ditrifluoromethyl-2-pyrimidinyl, 4-methyl-6-trifluoromethyl-2-pyrimidinyl, 2-methyl-4-pyrimidinyl, 2-trifluoromethyl-4-pyrimidinyl, 5-chloro-4-pyrimidinyl, 5-bromo-4-pyrimidinyl, 5-methyl-4-pyrimidinyl, 5-trifluoromethyl-4-pyrimidinyl, 6-methyl-4-pyrimidinyl, 6-trifluoromethyl-4-pyrimidinyl, 2-methyl-5-pyrimidinyl, 2-trifluoromethyl-5-pyrimidinyl, 4-methyl-5-pyrimidinyl, 4-trifluoromethyl-5-pyrimidinyl, 6-methyl-5-pyrimidinyl, 6-trifluoromethyl-5-pyrimidinyl, 2,4-dimethyl-5-pyrimidinyl, 2-methyl-4-trifluoromethyl-5-pyrimidinyl, 4-methyl-2-trifluoromethyl-5-pyrimidinyl, 2,4-ditrifluoromethyl-5-pyrimidinyl, 4,6-dimethyl-5-pyrimidinyl, 4-methyl-6-trifluoromethyl-5-pyrimidinyl, 4,6-ditrifluoromethyl-5-pyrimidinyl, 2,4,6-trimethyl-5-pyrimidinyl, 2,4-dimetryl-6-trifluoromethyl-5-pyrimidinyl, 2-methyl-4,6-ditrifluoromethyl-5-pyrimidinyl, 4,6-dimethyl-2-trifluoromethyl-5-pyrimidinyl, 4-methyl-2,6-ditrifluoromethyl-5-pyrimidinyl, 2,4,6-tri(trifluoromethyl)-5-pyrimidinyl;

3-methyl-2-pyrazinyl, 3-trifluoromethyl-2-pyrazinyl, 5-methyl-2-pyrazinyl, 5-trifluoromethyl-2-pyrazinyl, 6-methyl-2-pyrazinyl, 6-trifluoromethyl-2-pyrazinyl, 3,5-dimethyl-2-pyrazinyl, 3-methyl-5-trifluoromethyl-2-pyrazinyl, 5-methyl-3-trifluoromethyl-2-pyrazinyl, 3,5-ditrifluoromethyl-2-pyrazinyl, 3,6-dimethyl-2-pyrazinyl, 3-methyl-6-trifluoromethyl-2-pyrazinyl, 6-methyl-3-trifluoromethyl-2-pyrazinyl, 3,6-ditrifluoromethyl-2-pyrazinyl.

According to the present invention, there is further provided an anticoccidial drug composition containing at least one substituted 1,2,4-triazine-3,5-dione derivative having the above-mentioned general formula (I) or a salt thereof, as an active component.

The compound of the present invention having the general formula (I) can be obtained by, for example, cyclizing an intermediate compound having the following general formula (III):

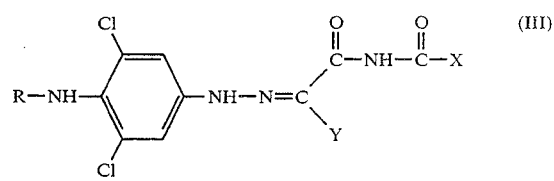

wherein R is the same as defined above, X is a suitable eliminating group such as an alkyloxy group, a halogen, etc, and Y is an electron attractive group which can be advantageously eliminated, such as a lower alkoxycarbonyl group, a cyano group, etc; in, for example, acetic acid with a metallic alkali salt of an organic acid (e.g., potassium acetate), and removing the group Y from the resulting compound having the following general formula (IV):

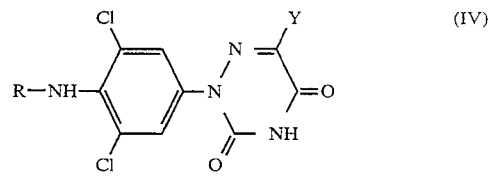

wherein each of R and Y is the same as defined above, in for example, acetic acid under a strong acidic condition such as hydrochloric acid to form a carboxylic acid derivative, followed by decarboxylation with thioglycolic acid. The intermediate compound (III) are known compounds as shown in, for example, J. Medicinal Chemistry, 26, 96–100 (1983).

The compound according to the present invention can be formulated into a preventive/curative medicament for poultry against coccidiosis in accordance with any conventional methods well known in the field of art. Namely, the compound of the present invention can be formulated into spreads, granules, suspensions, premixes, capsules, emulsions concentrates, tablets, and so forth, using the compound either as a single substance or with or without suitable carrier that are ordinarily used for this kind of medicaments, and using, at times, an excipient, a disintegrating agent, a sliding agent, a coating agent, and so forth.

The carriers usable in the preparations according to the present invention are not limited, in particular, so long as they can be added to the livestock feed or drinking water of poultry, and examples include water, milk sugar, cane sugar, talc, colloidal silica, pectin, wheat flour, rice bran, corn flour, soybean, oil cake, ground or powdered grain, and other commercial livestock feeds for poultry.

Although there are no specific limitations to the content or concentration of the active component, i.e., the compound (I) or the nontoxic salt thereof, the preferable content is 0.1 to 99% by weight, more specifically, 1 to 50% by weight.

When the compound according to the present invention is used as an additive to the feed, the dose is preferably such that at least 0.1 to 500 ppm and more preferably 0.5 to 100 ppm of the compound of the present invention, as calculated as the original compound, is contained in the livestock feed for poultry. When it is added to drinking water, the dose is about the half of the concentration in the livestock feed described above, and a sufficient effect can be obtained at such a concentration.

Furthermore, the compound according to the present invention can be used in combination with other medicaments for animals inclusive of known anticoccidial drugs for poultry, parasiticides, infection prophylaxis, growth promoters, and so forth.

As will be obvious from the later-appearing Test Example, the compound of the present invention exhibits higher anti-coccidium activities such as the restriction of the drop of a relative body weight increase ratio, the restriction of hematohezia, the decrease of number of oocyst (O.P.G) and the improvement in a cecitis lesion value, in chicks infected with coccidiostat, in comparison with salinomycin and clopidol, used as control anticoccidial drug. The compound of the present invention has a low toxicity as can be appreciated clearly from the data of the number of dead chicks, and can be therefore used as the preventive/curative agent for poultry such as chickens, turkeys, qualis and ducks against coccidiosis.

EXAMPLES

The present invention will now be further illustrated by, but is by no means limited to, the following Examples.

EXAMPLE 1

Synthesis of 2-[4-(5-chloro-2-pyridylamino)-3,5-dichlorophenyl]-1,2,4-triazine-3,5-(2H, 4H)-dione (Compound 1)

A 5.4 g amount of 4-(5-chloro-2-pyridylamino)-3,5-dichloroaniline was dissolved in a mixed solution of 4.4 ml of concentrated hydrochloric acid and 60 ml of acetic acid and, while this solution was cooled with ice, 1.4 g of an aqueous sodium nitrite solution was dropwise added, followed then by stirring for 30 minutes. Furthermore, a mixture of 3.5 g of sodium acetate and 3.2 g of ethyl N-cyanoacetylcarbamate was added, and the mixture was stirred at a room temperature for 2 hours. The reaction mixture was poured into water, and the resulting crystal was filtrated and washed with water to give 8.6 g of ethyl N-[{cyano-(3,5-dichloro-4-(5-chloro-2-pyridylamino)phenylhydrazynylidene)methyl}carbonyl]carbamate.

The compound obtained above was dissolved in 90 ml of acetic acid and, after 1.8 g of potassium acetate was added, the mixture solution was refluxed under heat for 3 hours. The reaction solution was concentrated and was then crystallized from water to yield 7.6 g of a crude crystal of 2-[3,5-dichloro-4-(5-chloro-2-pyridylamino)phenyl]-3,5-(2H, 4H)-dioxo-6-cyano-1,2,4-triazine. This cyclized compound was dissolved in a mixed solution of 25 ml of concentrated hydrochloric acid and 125 ml of acetic acid, and was refluxed under heat for 15 hours. The reaction solution was concentrated to the half volume, and the resulting crystal was filtrated and then washed with water to yield 5.9 g of 2-(3,5-dichloro-4-(5-chloro-2-pyridylamino)phenyl-1,2,4-triazine-3,5-(2H, 4H)-dione-6-carboxylic acid.

A 4.9 g amount of the above-prepared carboxylic acid was mixed with 10 ml of mercaptoacetic acid and refluxed under heat at 150° C. for 1.5 hours. The reaction solution was poured into water, and the resulting crystal was filtrated to yield 4.8 g of a crude crystal. This crude crystal was recrystallized from ethyl acetate-hexane to yield 3.9 g of the above compound (1).

EXAMPLE 2

Synthesis of 2-[3,5-dichloro-4-(5-methyl-2-pyridylamino)phenyl]-1,2,4-triazine-3,5-(2H, 4H)-dione (Compound 2)

A 0.6 g amount of the compound (2) identified above was obtained in the same manner as in Example 1 from 1.7 g of the starting material, i.e. 3,5-dichloro-4-(5-methyl-2-pyridylamino)aniline.

EXAMPLE 3

Synthesis of 2-[4-(3-chloro-5-trifluoromethyl-2-pyridylamino)-3,5-dichlorophenyl]-1,2,4-triazine-3,5-(2H, 4H)-dione (Compound 3)

A 1.1 g amount of the compound (3) identified above was obtained in the same manner as in Example 1 from 1.7 g of the starting material, i.e. 4-(3-chloro-5-trifluoromethyl-2-pyridylamino)-3,5-dichloroaniline.

EXAMPLE 4

Synthesis of 2-[3,5-dichloro-4-(3-pyridylamino)phenyl]-1,2,4-triazine-3,5-(2H, 4H)-dione (Compound 2)

A 0.9 g amount of the compound (4) identified above was obtained in the same manner as in Example 1 from 1.0 g of the starting material, i.e. 3,5-dichloro-4-(3-pyridylamino)aniline.

EXAMPLE 5

Synthesis of 2-[3,5-dichloro-4-(2-pyrimidinylamino)-phenyl]-1,2,4-triazine-3,5-(2H, 4H)-dione (Compound 5)

A 2.1 g amount of the compound (5) identified above was obtained in the same manner as in Example 1 from 2.0 g of the starting material, i.e. 3,5-dichloro-4-(2-pyrimidinylamino)aniline.

EXAMPLE 6

Synthesis of 2-[4-(5-chloro-2-pyrimidinylamino)-3,5-dichlorophenyl]-1,2,4-triazine-3,5-(2H, 4H)-dione (Compound 6)

A 1.1 g amount of the compound (6) identified above was obtained in the same manner as in Example 1 from 1.2 g of the starting material, i.e. 4-(5-chloro-2-pyrimidinylamino)-3,5-dichloroaniline.

EXAMPLE 7

Synthesis of 2-[4-(5-bromo-2-pyrimidinylamino)-3,5-dichlorophenyl]-1,2,4-triazine-(2H, 4H)-dione (Compound 7)

A 1.1 g amount of the compound (7) identified above was obtained in the same manner as in Example 1 from 1.2 g of the starting material, i.e. 4-(5-bromo-2-pyrimidinylamino)-3,5-dichloroaniline.

EXAMPLE 8

Synthesis of 2-3,5-dichloro-4-(5-methyl-3-isoxazolylamino)phenyl]-1,2,4-triazine-3,5-(2H, 4H)-dione (Compound 8)

A 0.9 g amount of the compound (8) identified above was obtained in the same manner as in Example 1 from 1.6 g of the starting material, i.e. 3,5-dichloro-4-(5-methyl-3-isoxazolylamino)aniline.

EXAMPLE 9

Synthesis of 2-[3,5-dichloro-4-(5-trifluoromethyl-1,3,4-thiadiazole-2-ylamino)phenyl]-1,2,4-triazine-3,5-(2H, 4H)-dione (Compound 9)

A 1.0 g amount of the compound (9) identified above was obtained in the same manner as in Example 1 from 1.5 g of the starting material, i.e. 3,5-dichloro-4-(5-trifluoromethyl-1,3,4-thiadiazole-2-ylamino)aniline.

The property (i.e., melting point) of these compounds are listed in Table 1.

TABLE 1

| Compound No. | R | melting point (mp) °C. |
| --- | --- | --- |
| 1 | 5-Cl-2-pyridyl | >250 |
| 2 | 5-$CH_3$-2-pyridyl | >250 |
| 3 | 3-Cl-5-$CF_3$-2-pyridyl | 219 |
| 4 | 3-pyridyl | 157–159 |
| 5 | 2-pyrimidinyl | >250 |
| 6 | 5-Cl-2-pyrimidinyl | >250 |
| 7 | 5-Br-2-pyrimidinyl | >250 |
| 8 | 5-$CH_3$-3-isoxazolyl | 243 (decomposed) |
| 9 | 5-$CF_3$-2-thiadiazolyl | >250 |

Next, the formulation Examples of the anticoccidial drug composition according to the present invention will be demonstrated.

EXAMPLE 10

Preparation of 100X powder (1)

One percent by weight of the compound 1 was well mixed with 99 wt. % of milk sugar to obtain the 100X powder. When in use, this powder was diluted with a feed to a predetermined concentration and could be used.

EXAMPLE 11

Preparation of 100X powder (2)

One percent by weight of the compound 3 was well mixed with 99 wt. % of cane sugar to obtain 100X powder. When in use, this powder was diluted with drinking water to a predetermined concentration and could be used.

EXAMPLE 12

Preparation of 10X powder Ten percent by weight of the compound 6 was well mixed with 90 wt. % of wheat flour to obtain 10X powder. When in use, this powder was diluted with a feed to a predetermined concentration, and could be used. The in vivo preventive effect of the anticoccidial drug composition for poultry according to the present invention was evaluated in the following way.

TEST EXAMPLE

Measurement of preventive/curative effect against coccidiosis in chicks

Five chicks of white leghorns of 7 to 10 days' age were grouped into groups, and a feed containing the specimen was dosed. Two days after the start of the dosage, the chicks were infected with 50,000 pcs/chick of the sporogenesitic Oocyst of the *Eimeria tenella*. The specimen was dosed continuously for nine days, and the degree of hematochezia, a survival ratio and a relative body weight increase ratio during that period were observed. Autopsy of the chicks was carried out at eighth day after the dose so as to observe the cecal lesion and to calculate a cecal lesion score.

The judgement standard of this test is listed below.
Relative body weight increase ratio:
This ratio was expressed by the following formula:
(body weight increase of test group)÷(body weight increase of non-infected control group)×100 (%)

Hematochezia:
The degree of hematochezia during the test period was evaluated by the following four stage:
—: No hematochezia was observed.
+: Light hematochezia was observed.
++: Medium hematochezia was observed.
+++: Hematochezia equivalent to that of the infected control group was observed.

Cecal lesion score:
The score was measured in accordance with the Merck determination method.

Autopsy of the surviving chicks was carried out on the eighth day after the infection, and the cecal lesion was observed with eye. The degree of the lesion was divided into 0 to 4 (0: no lesion to 4: critical), the strength was measured in this period, and the mean value of the five chicks was employed.

Number of Oocyst (O.P.G.):
By the number of oocyst (O.P.G.) existing in 1 g of feces on the sixth day after the infection.

The test result is tabulated in Table 2 in comparison with a Comparative Control Group treated with a known anticoccidial drug, an untreated Infected Control Group and an untreated Non-Infected Control Group.

TABLE 2

| Compound | Concentration (ppm) | Relative body weight increase ratio (%) | Number of dead chicks (dead/survival) | Hematochezia 4th day | 5th day | 6th day | 7th day | Oocysts per gram feces (O. P. G.) | Cecal lesion score |
| --- | --- | --- | --- | --- | --- | --- | --- | --- | --- |
| (infected control) | 0 | 40.8 | 0/5 | + | +++ | ++ | + | $2.70 \times 10^6$ | 4.0 |
| (non-infected control) | 0 | 100.0 | 0/5 | — | — | — | — | 0 | 0 |
| 1 | 20 | 96.9 | 0/5 | — | — | — | — | 0 | 0 |
|  | 10 | 100.0 | 0/5 | — | ± | + | — | 0 | 0.8 |
|  | 5 | 87.5 | 0/5 | — | + | ++ | + | 0 | 1.8 |
| 3 | 20 | 97.0 | 0/5 | — | — | — | — | 0 | 0 |

TABLE 2-continued

| Compound | Concentration (ppm) | Relative body weight increase ratio (%) | Number of dead chicks (dead/survival) | Hematochezia 4th day | 5th day | 6th day | 7th day | Oocysts per gram feces (O.P.G.) | Cecal lesion score |
|---|---|---|---|---|---|---|---|---|---|
| | 10 | 95.5 | 0/5 | — | — | — | — | 0 | 0 |
| | 5 | 98.5 | 0/5 | — | — | — | ± | 0 | 0.6 |
| 6 | 20 | 95.8 | 0/5 | — | — | — | — | 0 | 0.6 |
| | 10 | 102.8 | 0/5 | — | — | — | — | 0 | 0.6 |
| | 5 | 97.2 | 0/5 | — | ± | ++ | + | 0 | 2.6 |
| Salinomycin | 80 | 96.0 | 0/5 | — | — | — | — | <$10^3$ | 0.8 |
| | 60 | 82.0 | 0/5 | — | ++ | + | — | $1.56 \times 10^6$ | 2.4 |
| Clopidol | 125 | 105.1 | 0/5 | — | — | — | — | 0 | 0 |
| | 31.3 | 67.6 | 0/5 | ± | +++ | ++ | + | $1.56 \times 10^6$ | 4.0 |

As can be seen clearly from the result shown in Table 2, the compound according to the present invention exhibited the anticoccidial activity at a lower concentration than the known anticoccidial drug used for the control. Particularly, the number of Oocysts on the sixth day of the infection was 0(zero) even in the group infected with 5 ppm of the specimen. It thus became clear that the compound of the invention had a strong activity for preventing the infection of the individuals and also had the preventive action of the infection for other infected individuals.

As described above, the compound of the present invention has low toxicity and an extremely high anticoccidial activity. Since the discharge of oocysts into feces is not at all observed, the present invention can provide an effective anticoccidial drug composition.

We claim:

1. A substituted, 1,2,4-triazine-3,5-dione derivative of the formula (I) or a salt thereof:

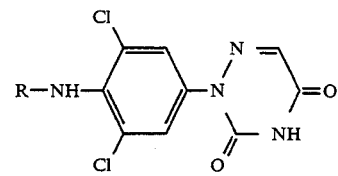

(I)

wherein R represents a 5- or 6-membered heterocyclic group selected from isoxazolyl, oxazolyl, thiadiazolyl, pyridyl, pyrimidinyl and pyrazinyl, which comprises 1 to 3 substituents selected from the group consisting of a halogen, a lower alkyl group and a halogenated lower alkyl group.

2. A substituted 1,2,4-triazine-3,5-dione derivative or a salt thereof, as claimed in claim 1, wherein said 5- or 6-membered heterocyclic group represents a pyridyl or pyrimidinyl group.

3. A substituted 1,2,4-triazine-3,5-dione derivative or a salt thereof, as claimed in claim 1, wherein R in the formula (I) represents 5-chloro-2-pyridyl, 3-chloro-5-trifluoromethyl-2-pyridyl, 5-chloro-2-pyrimidinyl, or 5-bromo-2-pyrimidinyl.

4. An anticoccidial drug composition comprising an anticoccidially effective amount of at least one compound according to claim 1, and a carrier therefor.

5. An anticoccidial drug composition as claimed in claim 4, wherein said 5- or 6- membered heterocyclic group represents a pyridyl or pyrimidinyl group.

6. An anticoccidial drug composition as claimed in claim 4, wherein R in the formula (I) represents 5-chloro-2-pyridyl, 3-chloro-5-trifluoromethyl-2-pyridyl, 5-chloro-2-pyrimidinyl, or 5-bromo-2-pyrimidinyl.

7. A method of preventing or treating coccidiosis in poultry comprising administering to a subject the substituted 1,2,4-triazine-3,5-dione derivative of formula (I) or a salt thereof according to claim 1 in an amount effective for preventing or treating poultry against coccidiosis.

8. The method according to claim 7, wherein 0.1 to 500 ppm of the substituted 1,2,4-triazine-3,5-dione derivative of formula (I) or a salt thereof is administered to the subject by addition to feed of the subject.

9. The method according to claim 8, wherein 0.5 to 100 ppm of the substituted 1,2,4-triazine-3,5-dione derivative of formula (I) or a salt thereof is administered.

10. The method according to claim 7, wherein 0.05 to 250 ppm of the substituted 1,2,4-triazine-3,5-dione derivative of formula (I) or a salt thereof is administered to the subject by addition to drinking water of the subject.

11. The method according to claim 10, wherein 0.25 to 50 ppm of the substituted 1,2,4-triazine-3,5-dione derivative of formula (I) or a salt thereof is administered.

* * * * *